Figure 1:
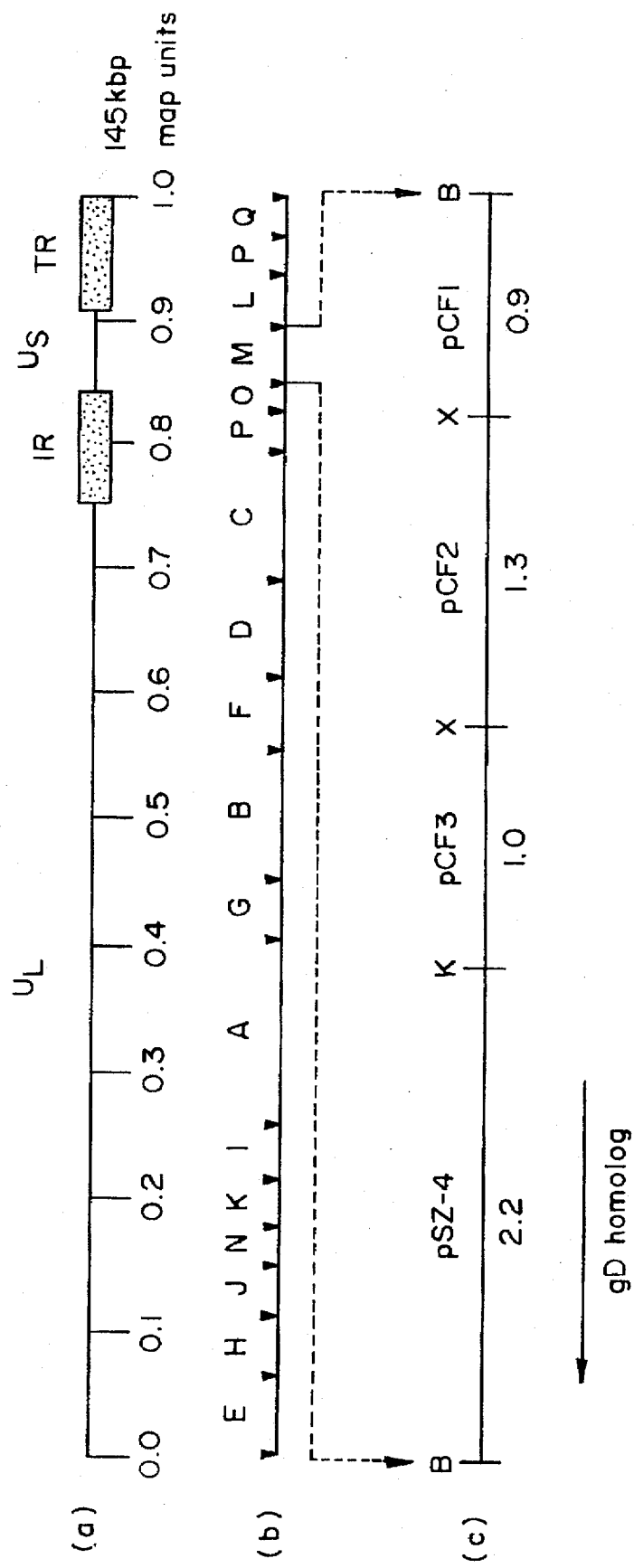

US005707629A

United States Patent [19]

O'Callaghan

[11] Patent Number: 5,707,629
[45] Date of Patent: Jan. 13, 1998

[54] IMMUNOGENIC COMPOSITION AGAINST EQUINE HERPESVIRUS TYPE 1

[75] Inventor: Dennis J. O'Callaghan, Shreveport, La.

[73] Assignee: Research Corporation Technologies, Inc., Tucson, Ariz.

[21] Appl. No.: 341,781

[22] Filed: Nov. 18, 1994

Related U.S. Application Data

[62] Division of Ser. No. 954,417, Sep. 30, 1992, Pat. No. 5,470,718, which is a continuation of Ser. No. 561,553, Aug. 1, 1990, abandoned.

[51] Int. Cl.$^6$ .......................... A61K 39/27; A61K 38/00; C07K 7/08; C07K 14/03
[52] U.S. Cl. ...................... 424/186.1; 530/324; 530/325; 530/326; 530/350; 424/229.1; 930/220
[58] Field of Search ................ 424/229.1, 186.1; 514/12; 530/395, 806, 826, 324, 325, 326, 350; 930/220

[56] References Cited

PUBLICATIONS

Allen et al. J. Virology 61:2454–2461, 1987.
Whittaker et al. J. General Virology 73:801–809, 1992.
Stokes, et al. (1989), "A Hamster Model of Equine Herpesvirus Type I (EHV-1) Infection; Passive Protection by Monoclonal Antibodies to EHV-1 Glycoproteins 13, 14 and 17/18," *J. Gen. Virol.* 70: 1173–83.
Guo, et al. (1990), "Coexpression by Vaccinia Virus Recombinants of Equine Herpesvirus I Glycoproteins gp13 and gp14 Results in Potentiated Immunity", *J. Virol.* 64: 2399–2406.
Shimizu, et al., (1989), "Monoclonal Antibodies with Neutralizing Activity to Equine Herpesvirus I," *Arch. Virol.* 104: 169–74.
Paoletti (1990), "Herpes Virus Recombinant Poxvirus Vaccine," *Chem Abstracts* 115(3): Abstract 23680d.
Audonnet, et al., (1990) "Equine Herpesvirus Type I Unique Short Fragment Encodes Glycoproteins with Homology to Herpes Simplex Virus Type 1 gD, gI and gE," *J. Gen. Virol.* 71: 2969–78.
Flowers et al., (1991) "Sequence Analysis of a Glycoprotein D Gene Homolog within the Unique Short Segment of the EHV-1 Genome," *Virology* 180: 175–84.
Bonass et al., (1991), "Identification of the EHV-1 SP17/18 as a Homologue of HSV-1 gD," Genbank Accession No. M60946.
Whalley, et al., (1990), "Identification and Comparative Sequence Analysis of a Gene in Equine Herpesvirus I with Homology to the Herpes Simplex Virus Glycoprotein D Gene," Genbank Accession No. M59773.

*Primary Examiner*—Mary E. Mosher
*Assistant Examiner*—Ali R. Salimi
*Attorney, Agent, or Firm*—Scully, Scott, Murphy & Presser

[57] ABSTRACT

The present invention is directed to a gene encoding an envelope glycoprotein of equine herpesvirus type 1 (EHV-1), the glycoprotein D (gD) gene, its gene product and antibodies directed against gD polypeptides. The envelope glycoproteins of herpesvirus are major targets of the immune response to herpesviral infection. Hence, an important aspect of this invention is directed towards a vaccine against EHV-1 and treatment of EHV-1 infection by anti-EHV-gD antibodies or antisera.

14 Claims, 6 Drawing Sheets

KpnI

| Sequence | Position |
|---|---|
| GGT ACC CGT TTA CGC CCT CGT ATC TAC GCT TAG AGT TCC GTG GTT AAA TGT | 51 |
| TAT TCC ACT AAC AAA AAT TAC TTG CGC TGC TTG CCC CAC GAA TCT AGT CGC | 102 |
| CGG CGA TGG GGT GGA CCT CAA CTC ATG TAC CAC CAA ATC AAC CAC AAT ACC | 153 |
| GTG TCC GGG CCA ACA GCG CAC CCA TAT TTT TTT CTC TGC GAA AGG GGA CAG | 204 |
| GGC TGT GTG TAT CAC ATC AGA ACT GGT GTC CCA GCC CAC AAT AAC TTG GTC | 255 |
| AGT TGG ATC AGA TAG GTT GCG TAA CGA TGG ATT TTC TCA GAC GTG GTA TGG | 306 |
| AAT ACA GCC CGG GGT GTG TGG TAT ACT GCG CAG CGA GGT TCG CAT TCA CCG | 357 |
| CAC CAC CTG GCG CTT TGG ATC AAC ATC AAA GGA CTA TCT CTG TGA GGT CAG | 408 |
| CGC ATC GGA CTC AAA GAC GAG CGA TTA CAA AGT GCT ACC CAA CGC CCA CTC | 459 |
| AAC TTC CAA CTT CGC TTT AGT GGC TGC GAC CAC GCT AAC AGT GAC AAT TTT | 510 |

```
                                                                              x
ATG CCT GCT GTG CTG CTT GTA CTG TAT GTT AAC CCG CCC CCG AGC GTC TGT         561
 M   P   A   V   L   L   V   L   Y   V   N   P   P   P   S   V   C          17 xxx           @@@@@@@@@
ATA TTA ACT CAA AAA TTA TCC CTT GGC CTT TAC AAC CAG TGG TGG CGT GTA         612
 I   L   T   Q   K   L   S   L   G   L   Y   N   Q   W   W   R   V          34

TGC AGA AGC GTG CCA CCG CCC TGG TAC GTG TTT TTC AAT AAA CGA AGC ATG         663
 C   R   S   V   P   P   P   W   Y   V   F   F   N   K   R   S   M          51

TCT ACC TTC AAG CTT ATG ATG GAT GGA CGT TTG GTT TTT GCC ATG GCA ATC         714
 S   T   F   K   L   M   M   A   G   R   L   V   F   A   M   A   I          68
                         ─────────────────────────────────────────
                                          SIGNAL
GCG ATC TTG AGC GTT GTG CTC TCT TGT GGA ACA TGC GAG AAA GCC AAG CGT         765
 A   T   L   S   V   V   L   S   C   G   T   C   E   K   A   K   R          85
 ─────────────────────────
        SEQUENCE
GCG GTT CGA GGA CGC CAG GAT AGG CCA AAG GAG TTT CCA CCA CCC CGC TAT         816
 A   V   R   G   R   Q   D   R   P   K   E   F   P   P   P   R   Y         102

AAC TAT ACA ATT TTA ACA AGA TAC AAC GCG ACT GCG CTA GCA TCA CCG TTT         867
 N   Y   T   I   L   T   R   Y   N   A   T   A   L   A   S   P   F         119

ATT AAC GAC CAA GTA AAA AAT GTT GAC TTG CGG ATT GTT ACT GCT ACG CGC         918
 I   N   D   Q   V   K   N   V   D   L   R   I   V   T   A   T   R         136

CCA TGT GAA ATG ATA GCG CTC ATC GCT AAG ACA AAC ATA GAC TCA ATC CTG         969
 P   C   E   M   I   A   L   I   A   K   T   N   I   D   S   I   L         153

AAG GAG CTG GCC GCT GCC CAA AAA ACT TAT TCC GCC AGA CTC ACC TGG TTT        1020
 K   E   L   A   A   A   Q   K   T   Y   S   A   R   L   T   W   F         170
```

FIG. 2A

```
AAA ATT ATG CCA ACG TGT GCA ACG CCT ATA CAC GAT GTT AGT TAT ATG AAA         1071
 K   I   M   P   T   C   A   T   P   I   H   D   V   S   Y   M   K          187

TGC AAC CCG AAG CTA TCA TTT GCA ATG TGT GAT GAG AGA TCA GAC ATA CTA         1122
 C   N   P   K   L   S   F   A   M   C   D   E   R   S   D   I   L          204

TGG CAA GCT AGT TTA ATT ACT ATG GCT GCT GAA ACT GAC GAT GAA CTT GGA         1173
 W   Q   A   S   L   I   T   M   A   A   E   T   D   D   E   L   G          221

CTT GTA CTG GCA GCC CCT GCA CAT TCT GCC TCG GGA CTG TAT CGC CGT GTT         1224
 L   V   L   A   A   P   A   H   S   A   S   G   L   Y   R   R   V          238

ATA GAA ATC GAC GGA AGG CGA ATT TAC ACG GAC TTT TCT GTA ACT ATT CCC         1275
 I   E   I   D   G   R   R   I   Y   T   D   F   S   V   T   I   P          255

AGT GAA CGG TGT CCG ATT GCC TTT GAG CTA AAC TTT GGC AAT CCG GAT CGG         1326
 S   E   R   C   P   I   A   F   E   L   N   F   G   N   P   D   R          272

TGT AAA ACT CCA GAG CAG TAC TCG CGG GGA GAA GTT TTT ACA CGT CGG TTT         1377
 C   K   T   P   E   Q   Y   S   R   G   E   V   F   T   R   R   F          289

CTT GGT GAA TTC AAC TTC CCA CAA GGA GAG CAT ATG ACA TGG GTG AAG TTC         1428
 L   G   E   F   N   F   P   Q   G   E   H   M   T   W   V   K   F          306

TGG TTC GTC TAC GAT GGT GGA AAC CTA CCA GTG CAG TTT TAT GAA GCC CAG         1479
 W   F   V   Y   D   G   G   N   L   P   V   Q   F   Y   E   A   Q          323

GCA TTC GCA AGA CCC GTG CCT CCG GAT AAC CAC CCT GGA TTT GAT TCT GTT         1530
 A   F   A   R   P   V   P   P   D   N   H   P   G   F   D   S   V          340

GAG TCG GAG ATT ACA CAA AAT AAA ACA GAC CCG AAA CCA GGC CAG GCG GAC         1581
 E   S   E   I   T   Q   N   K   T   D   P   K   P   G   Q   A   D          357
                         ─── ─── ───

CCC AAA CCC AAT CAG CCT TTT AAG TGG CCC AGC ATC AAA CAC TTG GTC CCA         1632
 P   K   P   N   Q   P   F   K   W   P   S   I   K   H   L   V   P          374

AGA CTC GAT GAG GTG GAT GAG GTC ATA GAG CCC GTA ACA AAG CCC CCA AAA         1683
 R   L   D   E   V   D   E   V   I   E   P   V   T   K   P   P   K          391

ACG TCT AAG AGC AAC TCT ACG TTT GTG GGC ATC AGC GTC GGT TTG GGT ATC         1734
 T   S   K   S   N   S   T   F   V   G   I   S   V   G   L   G   I          408
                 ─── ───                             ─────────────
                                                     MEMBRANE

GCC GGC CTA GTA TTG GTG GGC GTC ATT CTA TAC GTC TGC TTG CGT CGG AAG         1785
 A   G   L   V   L   V   G   V   I   L   Y   V   C   L   R   R   K          425
 ─── ─── ─── ─── ─── ─── ─── ─── ─── ─── ─── ─── ───
         SPANNING            DOMAIN
AAG GAA CTG AAA GTC TGC ACA GAA CGG CTT GAC TCG CCT ACG CTC GAC CTT         1836
 K   E   L   K   V   C   T   E   R   L   D   S   P   T   L   D   L          442
         *  *** **                       ++ +++ +
TAA GGA TGT TAA ATA TAC CCA GCT TCC GTA AAC AGT GTT GCG TAA CCT GCT         1887

CCA GAT TAA GCG AGG TTT TCC CTC TCA GCG ATC ACT TTT CAC CAC CGA AGA         1938

ACA GGC CCT CAT CGG TTT CCC TCC GTG TTT TCC CAT CCA TCT ATC AAC CA          1989

CTA CAT TTT CAT GGA GAA GGC GGA GGC TGC CGC AGT TGT TAT ACC CCT GTC         2040
```

FIG.2B

```
AGT TTC CAA CCC CAG CTA CCG TGG AAG CGG TAT GTC CGA CCA AGA AGT AAG                    2091

CGA AGA ACA ATC TGC TGG AGA TGC CTG GGT GTC TGC AGC AAT GGC AGC CGC                    2142

AGA GGC GGT GGC TGC TGC CGC TAC CTC CAC CGG AAT TGA TAA CAC TAA CGA                    2193
                                          BamHI
CTA CAC GTA CAC CGC TGC TTC TGA GAA TGG GGA TCC                                        2229
```

FIG.2C

```
EHV                              MPAVLLVLYVNPPPSVCILTQKLSLGLYNQWRVCRSVPPFWIVFFNKRS    50

PRV                              MLLAALLAALVARTILGADVDAVPAPIFP..PPAYPYIESWQ.LT.LTTVPS  48
                                 |   |         |           ||    || ||  ||           |
EHV  MSIFKLMMDGRLVFAMATAILSVVLSCGICEKAKRAVRGRQDRPKEFP..PPRYNYTILIR.YN.ATALAS       117
     |     |       |               |  |          ||| |         || |
     <- - - - - - - - - - - ->
HSV  MGGAAARLGAVILFVVIVGLHGVRSKYALVDASLKMADPNRFRGKDLPVLDQLIDPPGVRRVYHIQAGLPD        71
     <- - - - - - - - - ->  |||         ||           |                 |
                                  *                                    *
PRV  PFV.GPA.DV.YHIRPLEDPCGWALISDPQVDRLLNEAV..AHRRPTYRAHVAWYRIADCCAHLLYFIEY        114
     |    |      |   |  |  ||  |||   |   |  ||   |  |     ||    |  |    |
EHV  TFINDQVKNVDLRIVTAIRPCEMTALIAKINIDSILKELA..AAQK.TYSARLTWFKIMPTCATPIHDVSY       185
     ||           |  ||      ||      |        |          ||  ||  |||| |   |
HSV  PFQPPSL..PTTVYYAVLERACRSVLLNAPSEAPQIVRGASEDVRKQ.PYNLTIAWFRMGGNCAIPTTVMEY      140

*    *
PRV  ADCCDPRQVFGRCRRRTIPMWWIPSADYMFPIEDELGLIMVAPGRFNECCYRRLVSVDGVNILITDFMVA.LP    184
     ||   |   |   |         |  | ||||||| |      |||   | |||     |    | | | |
EHV  MKCNPKLSFAMCDERSDILWQASLTIMAAEIDDELGLVLAAPAHSASGLYRRVIEIDGRRIYIDFSVT.IP      255
           |   |    | |    |||   ||| ||            ||    ||    |    |  |  |
HSV  TECSYNKSLGACPIRTQPRWN.YYDSFSAVSEDNLGFLMHAPAFEIAGIYLRLVKINDWIETIQFILEHRA     210
        |    |   ||  ||        ||| || ||||  |||   ||   ||  |

*      *
PRV  ECCECPFARVDQHRIYKFGACWSDDSFKRG.VDVMR.FLIPF.YQQPPHREVNYWYRKNGRILPRAHAAA       252
     ||             |       ||| |||| |   |     |  |     |      | ||  | |
EHV  .SERCPIA.FELNFGNP.DRCKIPEQYSRGEVFIRR.FLGEFNFPQGEHMIWKFWFVYDGGNLPVQFYEA      322
     ||     |  |  |     |  |     |         |  |    | |
HSV  .KGSCKYA.LPLRI.PP.SACLSPQAVQGVTVDSIGMLPRF.IPENQRIV.AVYSLKIAGWHGPKAPYTS     275

PRV  TPYA...IDP.ARPSAGSPRPR.PRPRPRPRP.KPEPAPATP.A.PPDRLPEPATRDHAAGGRPTPRPPRPE   316
     |   |   |  |              | | |                |   |    |   |
EHV  QAFARPVPPDNHPGFDSVESETIQNKIDPKPGQADPKPNQPFKWPSIKHLVPRLDEVDEVIEPVIKPPKIS     393
     |  |                             |              ||      |     |  |  |
HSV  .TLLPPELSET.P..NATQPELAPEDPEDSALLEDPVGIVAPQIPRNWH.IPSIQDAATPYHPPATPNNMG    341

PRV  TPHRPFAPPAVVPSGWPQPAEPFQPRIPAAPGVSRHRSVIVGIGIAMGA                            365
     |  |
EHV  KSNSIFVGISVGLGIAGLVLVGVILYVCLRRKKELKVCIERLDSPILDL                           442
     |         |   |       |    |  |    |
HSV  LIAGA.VG.G.SL..LAALVICGIV.YW.MRRHIQ.KA.PKRIRLPHIRE                          382
```

FIG.3

IMMUNOGENIC COMPOSITION AGAINST EQUINE HERPESVIRUS TYPE 1

This is a divisional of a application Ser. No. 07/954,417, filed on Sep. 30, 1992, issued as U.S. Pat. No. 5,470,718 on Nov. 28, 1995, which is a file wrapper continuation of Ser. No. 07/561,553, filed on Aug. 1, 1990 abandoned.

FIELD OF THE INVENTION

Equine herpesvirus type 1 (EHV-1) can cause respiratory disease, abortions and neurological disorders in horses. The present invention is directed to a gene encoding an envelope glycoprotein of EHV-1, the glycoprotein D (gD) gene, its gene product and antibodies directed against the gD gene product. The envelope glycoproteins of herpesviruses are major targets of the immune response to herpesviral infection. Hence, another aspect of this invention is directed towards a vaccine against EHV-1 and treatment of EHV-1 infection with anti-gD antibodies.

BACKGROUND OF THE INVENTION

It is now recognized that the herpesvirus of horses, referred to as equine rhinopneumonitis (also called equine abortion virus, or EHV-1) is not a single herpesvirus but two genetically and antigenically distinct viruses, sometimes designated as subtypes 1 and 2 of EHV-1. EHV-1 subtype 1 (often called simple EHV-1) causes respiratory disease, spontaneous abortion in pregnant mares and occasionally, paralysis in horses. EHV-1 subtype 2 (also referred to as EHV-4) causes respiratory disease and only occasionally, abortions. The present invention is directed to a glycoprotein isolated from subtype 1 EHV-1 (hereafter referred to as EHV-1 in accordance with the International Committee on Taxonomy of Viruses at Edmonton, Canada in 1987).

Outbursts of EHV-1 infections in horses frequently occur in areas of concentrated horse breeding, particularly during the winter months. The incubation period of EHV-1 is from 2 to 10 days. Initial symptoms of infection include high fever for 1 to 7 days and discharge from the nostrils. White cell counts are generally depressed during the first few days of fever and may take a week or 10 days to recover. Diarrhea and enteritis, edema of the legs and tendovaginitis are not common in uncomplicated cases but do occur in complicated cases. All symptoms are worsened by forced exercise or work; recovery is complete in 1 to 2 weeks unless complications develop.

Reinfection may occur at intervals of 4 to 5 months or longer. These subsequent infections are usually asymptomatic and generally do not result in complications in adult horses. However, the disease has been known to breakout annually in young horses on farms where no new horses have been introduced, suggesting that adult horses can act as carriers. EHV-1 infection in young horses is often associated with weaning and assembling in winter quarter.

Infected mares may have no overt signs of infection at first, with the incubation time between nasal inoculation and abortion varying from 3 weeks to 4 months. The virus spreads readily by direct contact, fomites and aerosolized secretions. It may spread from one abortive mare to others, but evidence indicates that almost all mares on a farm are infected 1 to 4 months before abortion; hence, infection spreads rapidly, probably by aerosolized secretions or direct contact. Some foals infected prenatally reach full term and are born alive, but abortion is the normal outcome of EHV-1 infection in pregnant mares.

The herpesviruses are a family of structurally similar viruses. They have a double-stranded DNA genome characterized by short and long unique sequences of DNA ($U_S$ and $U_L$ respectively), and inverted repeats of DNA sequence which inverting in orientation, giving rise to the prototype and flank the unique sequences. The $U_S$ region of DNA is capable of inverted arrangements of the EHV-1 genome. All herpesviruses replicate within the nucleus of a host cell, and several members of the herpes family, if not all, are capable of becoming latent after establishing a primary infection and then initiating recurring, sometimes acute, infections.

Herpesviruses are not only similar in their gross morphology, but also at the molecular level. For example, general antisera against Herpes Simplex Virus type 1 (HSV-1) and EHV-1 have been used to demonstrate some minimal crossreaction between these viruses by complement fixation, gel diffusion, immunofluorescence and immunoprecipitation. However, HSV-1 has less than 5% DNA sequence identity with EHV-1 and specific antibodies to each virus do not cross-neutralize the other (Ludwig et al., 1971, Virology 45: 534–537). Despite this, the genome of ESV-1 appears to be functionally colinear with the genomes of HSV, pseudorabies virus (PRV) and varicella-zoster virus, as determined by molecular hybridization experiments (Davison et al., 1983, J. Gen. Virol. 64: 1927–1942). Analysis of the organization and function of the EHV-1 genome is therefore not only relevant for elucidating the mechanisms underlying EHV-1 infection, but also may identify key features of herpesvirus genomes by comparative molecular biology.

A number of major structural proteins have been identified in EHV-1 virions, typically by protein gel electrophoresis and through the use of antibodies directed against the intact EHV-1 virion. However, interest has centered on the structural glycoproteins due to their roles in the infectious process and their ability to invoke an immune response. In addition to several minor glycoproteins, eight high abundance glycoproteins have been identified in the envelope of purified EHV-1 virions. These glycoproteins have molecular masses of 200, 125, 95, 90, 68, 63, 45, and 41 kilodaltons (Perdue et al., 1974, Virology 59: 201–216; Turtinen et al., 1981, Am. J. Vet. Res. 42: 2099–2104), and are generally distinguished as glycoproteins by use of gp followed by the numbers 2, 10, 13, 14, 17, 18, 21, and 22a, respectively. Little is known about the antigenic or molecular structure of most of these glycoproteins. However the genes for six of these proteins have been mapped on the EHV-1 genome (gp2, gp10, gp13, gp14, gp17/18 and gp21/22a; Allen et al, 1987, J. Virol. 61: 2454–2461). All but gp 17/18 map within the long unique ($U_L$) region of the EHV-1 genome.

Two of these six glycoproteins have been identified as homologs of glycoproteins known in other herpesviruses, based on map position: gp13 corresponds to gC of HSV (and gIII of PRV) and gp14 corresponds to gB of HSV (and gII of PRV) (Allen et al. 1987, supra). The nucleotide sequences of EHV-1 gp13 and gp14 have been determined and the translated amino acid sequences of both have revealed significant homology to the corresponding HSV glycoproteins (Allen et al., 1988, J. Virol 62: 2850–2858; Whalley et al., 1989, J. Gen. Virol. 70: 383–394). The HSV gB glycoprotein, with extensive amino acid sequence identity to EHV-1 gp14, is required for virus entry and cell fusion and has been shown to invoke circulating antibodies as well as cell-mediated immune response. Because of its structural similarity the gp14 protein may have a similar role.

A genomic library of EHV-1 DNA exists together with a physical, restriction map of the EHV-1 genome (Henry et al., 1981, Virology 115: 97–114). Identification and characterization of EHV-1 glycoproteins by analysis of the DNA in the unique short ($U_S$) region of the EHV-1 genome has led to the discovery of a new EHV-1 glycoprotein (glycoprotein D).

There is a long standing need for safe, effective, long-acting, vaccines against EHV-1 infection. A number of EHV-1 vaccines are currently available (e.g. U.S. Pat. No. 4,110,433 to Purdy; U.S. Pat. No. 4,083,958 to Bryans), but are derived from live viruses. In addition, the EHV-1 vaccines currently available are generally acknowledged as being inadequate in spectrum and duration of protection (Doll, 1961, J. Am. Vet. Med. Assoc. 139: 1324–1330; Bryans, 1976. In *Equine Infectious Diseases IV, Proceedings of the Fourth International Conference on Equine Infectious Diseases*, T. J. Bryans and H. Gerber, eds., Princeton: Veterinary Publications: 83–92; Burrows, et al., 1984, Veterin. Rec. 114: 369–374; and Stokes et al., 1989, J. Gen. Virol. 70: 1173–1183). Thus, the present discovery provides new vaccines for EHV-1 protection having significant advantages over those of the prior art, since the use of live or attenuated viruses is eliminated.

SUMMARY OF THE INVENTION

The present invention is directed to isolated DNA encoding equine herpesvirus type 1, glycoprotein D (gD), which maps within the unique short ($U_S$) region of the EHV-1 genome (map units 0.865–0.884). The (gD) polypeptide is encoded by an open reading frame at nucleotides 511–1836, 661–1836, 679–1836, or 682–1836, as shown in FIG. 2. The gD polypeptide appears to have a cleaved signal sequence which yields a polypeptide encoded by nucleotides 739–1836, depicted in FIG. 2. The gD polypeptides, and antigenic peptides thereof, are useful in vaccines against EHV-1 and for the production of antibodies directed against the gD polypeptide.

Another aspect of the present invention provides an isolated nucleic acid encoding an EHV-1 gD polypeptide as described above, or a fragment thereof, and replicable expression vectors containing these nucleic acids.

A still further aspect of this invention is directed to transformed hosts such as prokaryotic microorganisms and cultured eukaryotic cells containing the replicable expression vectors encoding EHV-1 gD polypeptides.

Another aspect of this invention provides isolated, EHV-1 gD protein and antigenic EHV-1 gD peptides, especially in recombinant form.

A further aspect of this invention provides a vaccine composition for immunization against EHV-1 containing a gD polypeptide or antigenic portions thereof and a pharmaceutically acceptable carrier.

A still further aspect of this invention provides polyclonal and monoclonal antibodies directed against the EHV-1 glycoprotein D, hybridoma cell lines producing these monoclonal antibodies and methods of using these antibodies to detect EHV-1.

Yet another aspect of this invention is directed a method of treatment or prevention of EHV-1 infection via the antibodies directed against the EHV-1 gD protein, including treatment by passive immunization.

BRIEF DESCRIPTION OF THE DRAWINGS

FIG. 1 depicts the genomic map location of the EHV-1 gD gene. (a) The structure of the vital genome is shown with the unique long ($U_L$) region and unique short ($U_S$) segment depicted with the solid lines and the internal repeat (IR) and terminal re,eat (TR) segments represented by closed boxes. (b) The BamHI restriction map of the prototype arrangement of the EHV-1 genome is shown, and restriction sites are indicated with arrows. The 5.2 Kbp BamHI M fragment maps entirely within the $U_S$ at map position 0.869–0.884 in the prototype arrangement and at map position 0.865–0.872 in the inverted arrangement. (c) Expanded restriction map of the BamHI M fragment showing the positions of restriction cleavage sites employed in subcloning. Restriction sites are labeled as follows: B, BamHI; K, KpnI; X, XbaI. The position of the pSZ-4 open reading frame encoding gD polypeptides is indicated by the arrow.

FIG. 2 depicts the nucleotide sequence of the 2.2 Kbp BamHI/KpnI pSZ-4 clone and the amino acid sequence of the gD open reading frame (ORF). Numbers at the end of each row note the distance of the nucleotide (upper number) from the KpnI recognition sequence and the distance of the amino acid residue (lower number) from the first possible initiation methionine in this ORF. Features in the sequence are shown with the following symbols: o, CAAT box; x, TATA box; #, HSV ICP4 consensus binding site homolog; @, putative cis-regulatory AT-rich region; *, polyadenylation signal; +, GT-rich region following the polyadenylation signal. Strongly hydrophobic amino acids are underlined with one solid line, and potential glycosylation sites for the addition of N-linked oligosaccharides (N-X-S/T; Hubbard and Ivatt, 1981, Ann. Rev. Biochem. 50: 555–583) are underlined with dashed lines.

FIG. 3. Alignment of the amino acid sequences of the EHV-1 gD ORF with HSV-1 gD (McGeoch et al., 1985, J. Mol. Biol. 181: 1–13) and PRV glo50 (Petrovskis et al., 1986, J. Virol. 59: 216–223), using the FASTP algorithm of Lipman and Pearson (1985, Science 227: 1435–1440). Amino acid identity is denoted by vertical bars between the sequences. Matches between PRV and HSV residues are noted below the HSV sequence. The asterisks (*) indicate the conserved cysteine residues. The position of the signal peptide cleavage site for HSV gD-1 (Eisenberg et al., 1984, J. Virol. 49: 265–268) and the for EHV-1 are denoted by arrows.

FIG. 4. Hydropathicity analysis of the amino acid sequence of EHV-1 gD. The hydrophobicity and hydrophilicity characteristics of the EHV-1 amino acid sequence were determined using the Kyte and Doolittle (1982, J. Mol. Biol. 157: 105–132) algorithm and a 15 amino acid window. The vertical axis represents a relative hydrophobic score where values above −5 (midpoint value indicated by dashed line) are hydrophobic. The horizontal axis represents the amino acid number of the EHV-1 gD translated sequence.

DETAILED DESCRIPTION OF THE INVENTION

The present invention provides the EHV-1 gD gene, encoded by the open reading frame (ORF) indicated by the nucleotide sequence in FIG. 2 (nucleotides 511–1836). The EHV-1 gD gene lies within the unique short ($U_S$) region of the EHV-1 genome, and is identified by sequencing a 2.2 kilobase (kb) fragment of DNA lying within this region. This 2.2 kb fragment, obtained from a libary of EHV-1 genomic DNA (Henry et al. supra.), is located within the $U_S$ region as determined by restriction mapping (Henry et al., supra). No other EHV-1 glycoproteins mapping within the $U_S$ region have heretofore been fully characterized by sequence analysis. DNA sequence analysis of this 2.2 Kb BamHI/KpnI fragment revealed an ORF whose translated sequence exhibits significant homology to glycoprotein D (gD) of herpes simplex virus (HSV) types 1 and 2 and to pseudorabies virus IPRV) glycoprotein 50, the gD equivalent (FIG. 2 and FIG. 3). The ORF of EHV-1 gD gene is capable of encoding several polypeptides all of which are contemplated by the present invention. If translation initiates at the first in-frame ATG at nucleotides 511–513 depicted in FIG. 2, a gD polypeptide having 442 amino acids and a calculated molecular weight of 49,904 is produced. Likewise, if translation initiates at the second, third or fourth in-frame ATG's (nucleotides 661–663, 679–681 or 682–684, respectively) then gD polypeptides having 393, 387 or 386 amino acids, respectively, are produced. Cleavage of a predicted signal sequence yields a mature EHV-1 gD polypeptide encoded by amino acids 77–442 (367 amino acids). The skilled artisan can identify and isolate a DNA encoding any of these gD polypeptides.

The fourth in-frame ATG at nucleotides 682–684 serves as a preferred initiation codon for several reasons: 1) the sequences neighboring this ATG comply most favorably with the sequence motif of an initiation codon according to Kozak's rules (Kozak, 1980, Cell 22: 7–8; Kozak, 1983, Microbiol. Rev. 47: 1045; Kozak 1986, Cell 44: 283–292); 2) residues following this methionine have the most likely signal sequence based on hydropathicity and a probable signal sequence cleavage site after residue number 19; 3) this gD polypeptide is 386 amino acids (a.a.) in size (43,206 molecular weight) which compares favorably to the size of the gD polypeptides of HSV-1 (394 a.a.), HSV-2 (394 a.a.), and PRV (402 a.a.); and 4) the relative positions of the 5' regulatory elements, namely the CAAT sequence at 502–505 and the TATA box at 561–564, suggest that transcription is initiated downstream of the first ATG. The nucleotide sequence of the gD gene reveals a complete transcriptional unit including CAAT and TATA elements and signals for polyadenylation. The gD polypeptide exhibits features typical of a transmembrane protein: a hydrophobic N-terminal signal sequence followed by a probable signal sequence cleavage site, four potential N-linked glycosylation sites, and a hydrophobic membrane-spanning domain near the carboxyl terminus followed by a charged membrane anchor sequence. Hence, the present invention provides a complete DNA sequence for the entire EHV-1 gD gene and allows identification of the EHV-1 gD polypeptides encoded in the identified ORF.

The present invention provides the EHV-1 gD gene on a 2.2 kb BamHI/KpnI fragment cloned into pUC19, to create pSZ-4.

Another aspect of the present invention provides replicable expression vectors allowing regulated expression of a EHV-1 gD polypeptide. Replicable expression vectors as described herein are generally DNA molecules engineered for controlled expression of a desired gene, especially high level expression where it is desirable to produce large quantities of a particular gene product, or polypeptide. The vectors encode promoters and other sequences to control expression of the gene being expressed, and an origin of replication which is operable in the contemplated host. Preferably the vectors are plasmids, bacteriophages, cosmids or viruses. Any expression vector comprising RNA is also contemplated.

Sequence elements capable of effecting expression of a gene product include promoters, enhancer elements, transcription termination signals and polyadenylation sites. Promoters are DNA sequence elements for controlling gene expression, in particular, they specify transcription initiation sites. Prokaryotic promoters that are useful include the lac promoter, the trp promoter, and $P_L$ and $P_R$ promoters of lambda and the T7 polymerase promoter. Eukaryotic promoters are especially useful in the invention and include promoters of vital origin, such as the baculovirus polyhedrin promoter, the vaccinia virus hemagglutinin (HA) promoter, SV40 late promoter, the Moloney Leukemia Virus LTR, and the Murine Sarcoma Virus (MSV) LTR. Yeast promoters and any promoters or variations of promoters designed to control gene expression, including genetically-engineered promoters are also contemplated. Control of gene expression includes the ability to regulate a gene both positively and negatively (i.e., turning gene expression on or off) to obtain the desired level of expression.

One skilled in the art has available many choices of replicable expression vectors, compatible hosts and well-known methods for making and using the vectors. Recombinant DNA methods are found in any of the myriad of standard laboratory manuals on genetic engineering (see for example Sambrook et al., 1989, *Molecular Cloning: A Laboratory Approach*, 2nd edition, Cold Spring Harbor Laboratory Press, Cold Spring Harbor, N.Y.).

The replicable expression vectors of the present invention can be made by ligating part or all of the EHV-1 gD coding region in the proper orientation to the promoter and other sequence elements being used to control gene expression. For example, a DNA fragment encoding gD nucleotides 511–1839 (depicted in FIG. 2) may be operably linked, by ligation, downstream of a promoter, thereby allowing expression of a 442 amino acid gD polypeptide. Similarly, ligation of DNA fragments encoding gD nucleotides 661–1839, 679–1839, or 682–1839 downstream of a promoter allows gD polypeptides of 393 amino acids, 387 amino acids or 386 amino acids to be expressed. This juxtapositioning of promoter and other sequence elements with gD polypeptide coding region allows the production of large amounts of the gD polypeptide useful, not only as a vaccine against EHV-1 infection, but also for anti-gD antibody production and for analysis of the function of gD during EHV-1 infection.

Preferred vectors of the present invention are derived from eukaryotic sources. Expression vectors that function in tissue culture cells are especially useful, but yeast vectors are also contemplated. These vectors include yeast plasmids and minichromosomes, retrovirus vectors, BPV (bovine papilloma virus) vectors, vaccinia virus vectors, baculovirus vectors, SV40 based vectors and other viral vectors. Baculovirus vectors and retrovirus vectors (e.g., murine leukemia viral vectors) and preferred. Tissue culture cells that are used with eukaryotic replicable expression vectors include *S. frugiperda* cells, VERO cells, MRC-5 cells, SCV-1 cells, COS-1 cells, NIH3T3 cells, mouse L cells, HeLa cells and such other cultured cell lines known to one skilled in the art.

The present invention also contemplates prokaryotic vectors that are suitable as cloning vectors or as expression vectors for EHV-1 gD polypeptides, including bacterial and bacteriophage vectors that can transform such hosts as *E. coli, B. subtilis, Streptomyces sps*. and other microorganisms. Many of these vectors are based on pBR322 including pUC19 and pGEM-7Zf (commercially available from Promega, Madison, Wis.) and are well known in the art. Bacteriophage vectors that are used in the invention include lambda and M13.

In one embodiment the EHV-1 gD gene is inserted into a lambda gt11 expression vector (Sambrook et al., 1989, *Molecular Cloning: A Laboratory Manual* Vol. 2, Cold Spring Harbor Laboratory Press: 12.1–12.44). Lambda gt11 is constructed to allow insertion of foreign DNA into the structural gene for beta-galactosidase, thereby producing a beta-galactosidase-foreign-protein fusion protein, under the control of the lac promoter. Such a fusion protein is easily isolated, for example, by using commercially available anti-beta-galactosidase antibodies. The gD-beta-galactosidase fusion protein can then be used to generate antibodies against the EHV-1 gD protein. As an alternative prokaryotic expression system, the pKK223-3 expression vector, can provide high levels of EHV-1 gD expression in E. coli. This vector contains the strong trp-lac (tac) promoter which is IPTG inducible. (deBoer et al., 1983, Proc. Natl. Acad. Sci. USA). A major advantage of the pKK223-3 expression vector is that an intact EHV-1 gD polypeptide is expressed rather than a beta-galactosidase fusion protein.

In another preferred embodiment, the EHV-1 gD protein of the present invention is expressed in a baculovirus expression system. This system provides baculovirus expression vectors into which EHV-1 gD DNA encoding an EHV-1 gD polypeptide can be inserted downstream of a strongly transcribed promoter. When cultured in insect cells, the recombinant baculovirus can provide stable expression of high levels of extracellular or intracellular polypeptide. Baculovirus expression vectors and their use are reviewed in Luckow et al. (1988, Bio/Technology6: 47–55). A particular advantage of this system is its similarity to higher eukaryotes with regard to protein modification, processing and transport. Thus, recombinant-derived eukaryotic proteins will be processed and glycosylated in a manner important for obtaining a native protein conformation and, hence, maximal biological activity.

A further aspect of the present invention is directed to an isolated EHV-1 gD polypeptide, especially a recombinant gD polypeptide. A gD polypeptide can be obtained from virally-infected cultured cells, from vitally-infected animals or from microorganisms or cells transformed with an expression vector encoding a gD polypeptide. A process of preparing a recombinant EHV-1 gD polypeptide includes cultivating the microorganism or cell transformed with an EHV-1 gD recombinant nucleic acid for a time and under conditions sufficient to produce a gD polypeptide and then recovering the gD polypeptide. Purification of a gD polypeptide is achieved by conventional purification techniques such as ammonium sulfate precipitation, column chromatography, affinity chromatography and the like. During purification, the gD polypeptide is identified by SDS-polyacrylamide gel electrophoresis, or by standard immunodetection techniques, such as immunoblotting or immunaprecipitation.

Antibodies can be used to purify an EHV-1 gD polypeptide. Antibodies are highly specific and are especially useful for isolating specific antigens (proteins) that represent only minor components of complex mixtures such as cell lysates. The lambda gt11 expression system described above provides a fusion protein of beta-galactosidase and EHV-1 gD proteins. This fusion protein can be purified by passage of a cell lysate containing the fusion protein over an anti-beta-galactosidase immuno-affinity column. The anti-beta-galactosidase antibodies bound to the column matrix bind the fusion protein. Any impurities can be washed off the column and the fusion protein can be eluted by changes in pH, or by use of detergents, chaotropic agents or organic solvents. Immunoaffinity purification techniques are well known in the art (see, for example, Harlowe, et al., 1988, Antibodies: A Laboratory Manual, Cold Spring Harbor Labortory Press: 511–552). The purified EHV-1 gD fusion protein can be used to obtain antibodies specific for the EHV-1 gD protein. These anti-EHV-1 gD antibodies in turn allow immunoaffinity purification of the non-fusion EHV-1 gD protein or peptides thereof.

Another embodiment of the present invention provides polyclonal antibodies directed against the EHV-1 protein or peptides encoding a portion of an EHV-1 polypeptide. The antibodies are useful for passive immunization of animals infected with EHV-1, and for the purification of EHV-1 gD polypeptides. Antibodies can be generated by using an entire EHV-1 gD polypeptide as an antigen or by using short peptides encoding a portion of an EHV-1 gD polypeptide, as antigens. Computer analysis of the gD polypeptide amino acid sequence was used to identify the following peptide sequences as being strongly antigenic epitopes for all gD polypeptides; subsequent analysis has confirmed this. Peptide 1 is located at amino acid residues 80–98, while Peptide 2 is located at amino acid residues 343–361 as depicted in FIG. 2. Peptide 2 has an additional cysteine residue at its carboxy terminus to allow coupling to a protein carrier.

The following peptides are preferred immunogens for generating antibodies:

Peptide 1 (EHV-1 gD nucleotides 748–804):

NH$_2$-Cys-Glu-Lys-Ala-Lys-Arg-Ala-Val-Arg-Gly-Arg-Gln-Asp-Arg-Pro-Lys-Glu-Phe-Pro-COOH

Peptide 2 (EHV-1 gD nucleotides 1537–1593):

NH$_2$-Glu-Ile-Thr-Gln-Asn-Lys-Thr-Asp-Pro-Lys-Pro-Gly-Gln-Ala-Asp-Pro-Lys-Pro-Asn-Cys-COOH

Polyclonal antibodies directed against an EHV-1 gD polypeptide or antigenic peptide thereof are prepared by injection of a suitable animal with an immunogenic amount of the peptide or antigenic component, collecting serum from the animal, and testing sera for the desired reactivity. If necessary, specific sera can be isolated by any of the known immunoadsorbent techniques. Detailed protocols for antibody production are provided in Harlow, E. et al. Antibodies: A Laboratory Manual, Cold Spring Harbor Press, N.Y., 1988.

Another embodiment of the present invention provides monoclonal antibodies. Monoclonal antibodies are preferred because large quantities of antibodies, all of similar reactivity, are produced. The preparation of hybridoma cell lines for monoclonal antibody-production is done by fusing an immortal cell line with antibody-producing lymphocytes from an immunized animal. This can be done by techniques which are well known to those who are skilled in the art. (See, for e5 example, Harlow, E. and Lane, D., Antibodies: A Laboratory Manual, Cold Spring Harbor Press, 1988; or Douillard, J. Y. and Hoffman, T., "Basic Facts About Hybridomas", in Compendium of Immunology Vol. II, L. Schwartz (Ed.), 1981.)

Unlike the preparation of polyclonal sera, the choice of animal for monoclonal antibody preparation is dependent on the availability of appropriate immortal cell lines capable of fusing with the antibody-producing lymphocytes derived from the immunized animal. Mouse and rat have been the animals of choice for hybridoma technology and are preferably used. For the purpose of making the monoclonal antibodies of the present invention, the animal of choice may be injected with from about 0.01 mg to about 20 mg of purified EHV-1 gD antigen. Typically the antigen is emulsified in an adjuvant to stimulate general immune responses. Boosting injections are generally also required. Lymphocytes can be obtained by removing the spleen or lymph nodes of immunized animals in a sterile fashion, and are fused to immortalized cells. A number of immortalized cell lines suitable for fusion have been developed, and the choice of any particular line is directed by any one of a number of criteria such as speed, uniformity of growth characteristics, deficiency of its metabolism for a component of the growth medium, and potential for good fusion frequency. Intraspecies hybrids, particularly between like strains, work better than interspecies fusions. Several cell lines are available, including mutant selected for the loss of ability to create myeloma immunoglobulin. Included among these are the following mouse myeloma lines: X63-Ag 8.653, $MPC_{11}$-X45-6TG, P3 NS1/1-Ag4-1, P3-X63-Ag14 (all BALB/C derived), Y3'Ag1.2.3 (rat), and U266 (human). X63-Ag8.653 cells are preferred.

The fused cell colonies are tested for the presence of antibodies that recognize EHV-1 gD polypeptides. Detection of monoclonal antibodies can be performed using an assay where the antigen is bound to a solid support and allowed to react to hybridoma supernatants containing the putative antibodies. The presence of antibodies may be detected by "sandwich" techniques using a variety of indicators. Most of the common methods are sufficiently sensitive for use in the range of antibody concentrations secreted during hybrid growth.

Cloning of hybrid cells can be carried out after 20–25 days of cell growth in selected medium. Cloning can be performed by cell limiting dilution in fluid phase or by directly selecting single cells growing in semi-solid agarose. For limiting dilution, cell suspensions are diluted serially to yield a statistical probability of having only one cell per well. For the agarose techniques, hybrids are seeded in a semisolid upper layer, over a lower layer containing feeder cells. The colonies from the upper layer may be picked up and eventually transferred to wells.

Antibody-secreting hybrid cells can be grown in various tissue culture flasks, yielding supernatants with variable concentrations of antibodies. In order to obtain higher concentrations, hybrid cells may be transferred into animals to obtain inflammatory ascites. Antibody-containing ascites can be harvested 8–12 days after intraperitoneal injection. The ascites contain a higher concentration of antibodies but include both monoclonals and immunoglubulins from the inflammatory ascites. Antibody purification may be achieved by, for example, affinity chromatography.

The present invention is also directed to the detection of EHV-1 infection by immunological techniques using antibodies directed against EHV-1 gD polypeptides. A method is provided for diagnosing EHV-1 infection by contacting a blood or serum sample of an individual to be tested with an antibody directed against an EHv-1 gD polypeptide, or an antigenic fragment thereof, for a time and under conditions sufficient to form an antigen-antibody complexing and detecting a resultant antigen-antibody complex.

The presence of gD polypeptides in horse's blood sample, and therefore the virus, can be detected utilizing antibodies prepared as above, either monoclonal or polyclonal, in virtually any type of immunoassay. A method for detecting EHV-1 includes contacting a test sample with an antibody directed against an EHV-1 gD polypeptide, or an antigenic peptide thereof, for a time and under conditions sufficient to form an antigen-antibody complex, and detecting the resultant antigen-antibody complex. A wide range of immunoassay techniques are available as can be seen by reference to Harlow, et al. (*Antibodies: A Laboratory Manual*, Cold Spring Harbor Press, 1988) and U.S. Pat. Nos. 4,018,043 and 4,424,279. This, of course, includes both single-site and two-site, or a "sandwich" of the non-competitive types, as well as in traditional competitive binding assays. Sandwich assays are among the most useful and commonly used assays. A number of variations of the sandwich assay technique exist, and all are among the most useful and commonly used assays. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen binary complex, a second antibody, labeled with a reporter molecule capable of producing a detectable signal is then added and incubated, allowing time sufficient for the formation of a ternary complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of antigen. Variations on the forward assay include a simultaneous assay, in which both the sample to be tested and the reporter conjugated antibody are first combined, incubated and then added to the unlabeled surface bound antibody. These techniques are well known to those skilled in the art, and the possibly of minor variations will be readily apparent. As used herein, "sandwich assay" is intended to encompass all variations on the basic two-site technique.

EHV-1 gD polypeptides may also be detected by a competitive binding assay in which a limiting amount of antibody specific for the gD polypeptides is combined with specified volumes of samples containing an unknown amount of the gD polypeptides and a solution containing a known amount of the detectably labeled, e.g. radio-labeled, gD polypeptides. Labeled and unlabeled molecules then compete for the available binding sites on the antibody. Phase separation of the free and antibody-bound molecules allows measurement of the amount of label present in each phase, thus indicating the amount of antigen or hapten in the sample being tested. Numerous variations on this general competitive binding assay, are known to the skilled artisan and are contemplated by the present invention.

In any of the known immunoassays, for practical purposes, one of the antibodies or the antigen may be bound to a solid phase, and a second molecule, either the second antibody in a sandwich assay, or, in a competitive assay, the known amount of antigen, may bear a detectable label or reporter molecule in order to allow detection of an antibody-antigen reaction. When two antibodies are employed, as in the sandwich assay, it is only necessary that one of the antibodies be specific for an EHV-1 gD polypeptide or its antigenic components. The following description provides the methodology for performing a typical forward sandwich assay; however, the general techniques are to be understood as being applicable to any of the contemplated immunoassays.

In the typical forward sandwich assay, a first antibody having specificity for the EHV-1 gD protein or its antigenic components is either covalently or passively bound to a solid surface. The solid surface is typically glass or a polymer, the most commonly used polymers being cellulose, polyacrylamide, nylon, polystyrene, polyvinyl chloride or polypropylene. The solid support may be in the form of tubes, beads, discs or microplate, or any other surface suitable for conducting an immunoassay. The binding processes are well-known in the art and generally consist of cross-linking, covalently binding or physically adsorbing the molecule to the insoluble carrier. Following binding, the polymer-antibody complex is washed in preparation for the test sample. An aliquot of the sample to be tested is then added to the solid phase complex and incubated at 25° C. (or other suitable temperature) for a period of time sufficient to allow binding of any antigen. The incubation period will vary but will generally be in the range of about 2–40 minutes. Following the incubation period, the antibody-antigen solid phase is washed and dried and incubated with a second antibody also specific for the gD protein or an antigenic region thereof. The second antibody is linked to a reporter molecule which is used to indicate the binding of the second antibody to the hapten. By "reporter molecule", as used in the present specification and claims, is meant a molecule which, by its chemical nature, provides an analytically identifiable signal which allows the detection of antigen-bound antibody. Detection may be either qualitative or quantitative. the most commonly used reporter molecules in this type of assay are either enzymes, fluorophores or radionuclide containing molecules. In the case of an enzyme immunoassay, an enzyme is conjugated to the second antibody, generally by means of glutaraldehye or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphates, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, D followed by emission of the light at a characteristic color, visually detectable with a light microscope. As above, the fluorescent labeled antibody is allowed to bind to the first antibody-antigen complex. After washing off the unbound reagent, the remaining ternary complex is then exposed to the light of the appropriate wavelength, the fluorescence observed indicates the presence of the antigen of interest. Immunofluorescence techniques are both very well established in the art. However, other reporter molecules, such as radioisotopes, chemiluminescent or bioluminescent molecules, can also be employed. It is readily apparent to the skilled technician how to vary the procedure to suit the required purpose.

In another embodiment, the antibodies directed against EHV-1 gD polypeptides are incorporated into a kit for the detection of EHV-1 infection. Such a kit may encompass any of the detection systems contemplated and described herein, and may employ either polyclonal or monoclonal antibodies directed against EHV-1 gD polypeptides or antigenic regions thereof. Both antibodies complexed to a solid surface described above or soluble antibodies are contemplated for use in a detection kit. The kit can be compartmentalized and includes at least one container containing primary anti-EHV-1 gD antibodies and another container containing secondary antibodies covalently bond to a reporter molecule, such that the secondary antibodies are capable of detecting the first antibodies or are themselves directed against EHV-1 gD. For example, one contemplated kit is compartmentalized and has the following components: the first container contains killed EHV-1 virus or EHV-1 gD polypeptides as a solution, or bound to a solid surface, to act as a standard or positive control, the second container contains anti-EHV-1-gD primary antibodies either free in solution or bound to a solid surface, a third container contains a solution of secondary antibodies covalently bound to a reporter molecule which are reactive against either the primary antibodies or against a portion of a gD polypeptide not reactive with the primary antibody. A fourth or fifth container contains a substrate, or reagent, appropriate for visualization of the reporter molecule.

The subject invention therefore encompasses anti-EHV-1-gD antibodies. EHV-1 gD antibodies are useful for purification of the EHV-1 gD protein as well as for the detection and study of the EHV-1 virus.

Another embodiment of the present invention provides pharmaceutical compositions of the EHV-1 gD protein or portions thereof, or of anti-EHV-1 gD antibodies.

One important embodiment of the present invention provides the purified EHV-1 gD protein or peptide portions thereof as a vaccine against EHV-1. The vaccine includes an immunogenic amount of an EHV-1 gD polypeptide or an antigenic peptide thereof and pharmaceutically acceptable inert ingredients commonly used in vaccinations. The effective dosage of this vaccine is about 0.5 µg to about 2000 mg of antigen per kilogram of body weight. Boosting regiments may be required and the dosage regimen can be adjusted to provide optimal immunization. The vaccination of a mare prior to breeding and again during her pregnancy may prevent abortions caused by EHV-1. Other horses can be vaccinated, for example, about once a year. Foals can be vaccinated shortly after birth. Vaccinations can be administered parenterally or extra-parenterally to the mucosal surfaces of the body. The intramuscular route of innoculation is preferred.

Another embodiment of the present invention contemplates the treatment or prevention of EHV-1 infection by passive immunization with anti-EHV-1 gD antibodies or horse anti-EHV-1 gD anti-serum. Pharmaceutical compositions for passive immunization include an amount of anti-EHV-1 gD antibody or antiserum effective in the treatment of EHV-1 infection, and particularly, effective in preventing abortion in EHV-1 infected pregnant mares. The dosage of anti-EHV-1 gD anti-serum may be from about 0.01 microliters to about 0.1 milliliters per kilogram of body weight. The dosage of anti-EHV-1-gD antibodies depends upon the efficacy and titer of the antibodies but may be from about 0.5 µg to about 2000 mg antibody protein per kilogram of body weight. The dosage regimen can be adjusted to provide the optimum therapeutic response. For example, if a horse is exposed to EHV-1 or if a horse (particularly a pregnant mare) becomes infected with EHV-1 several divided does can be administered daily or a single daily dose can be proportionally reduced or increased as indicated by the exigencies of the therapeutic situation.

The active compounds for vaccination or passive immunization may be administered in a convenient manner such as by intraveneous (where water soluble), intramuscular, subcutaneous, intranasal, or intradermal routes. Intramuscular administration is a preferred method of administration but other methods are also contemplated by the present invention. In order to administer EHV-1 gD protein or anti-EHV-1 gD antibodies by other than parenteral administration, they should be coated, or administered with, a material to prevent inactivation. For example, EHV-1 gD protein or anti-EHV-1 gD antibodies may be administered in an adjuvant, co-administered with enzyme inhibitors or administered in liposomes. Adjuvants contemplated herein include resorcinols, non-ionic surfactants such as polyoxyethylene oleyl ether and n-hexadecyl polyethylene ether.

The active compounds may also be administered parenterally or intraperitoneally. Dispersions can also be prepared in glycerol, liquid polyethylene glycols, and mixtures thereof, and in oils. Under ordinary conditions of storage and use, these preparations can contain a preservative to prevent the growth of microorganisms.

The pharmaceutical forms suitable for injectable use include sterile aqueous solutions (where water soluable) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thimerosal, and the like. In many cases it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient form previously sterile-filtered solution thereof.

It is especially advantageous to formulate parenteral compositions in dosage unit form for ease of administration and uniformity of dosage. Dosage unit form as used herein refers to physically discrete units suited as unitary dosages for the mammalian subjects to the treated; each unit containing a predetermined quantity of the active material calculated to produce the desired therapeutic effect in association with the required pharmaceutical carrier. The specification for the novel dosage unit forms of the invention are dictated by and directly depend on (a) the unique characteristics of the active material and the particular therapeutic effect to be achieved, and (b) the limitations inherent in the art of compounding such active material for the treatment of disease.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 10 µg to about 2000 mg/ml of carrier. In the case of compositions containing supplementary active ingredients, the dosages are determined by reference to the usual dose and manner of administration of the said ingredients.

As used herein "pharmaceutically acceptable carrier" includes any and all solvents, dispersion media, coatings, antibacterial and antifungal agents, isotonic and adsorption delaying agents, and the like. The use of such media gents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

Hence, the above pharmaceutical compositions provide therapeutically administrable forms of an anti-EHV-1 vaccine, and anti-EHV-1-gD antibodies. The vaccine is useful for long-term prevention of EHV-1 infection while the anti-sera and antibodies may be used for short-term prevention and treatment of EHV-1 infection.

The Examples serve to further illustrate the invention.

EXAMPLE 1

Viral and Bacterial Strains

EHV-1 (Kentucky A strain) was propogated in mouse L-M cells (O'Callaghan et al., 1968, Virology 36: 104–114; Perdue et al., 1974, Virology 59: 210–216). Extracellular virions purified from infectious supernatants were used as the source of vital DNA (Cohen et al., 1975, Virology 68: 561–565). All plasmids were maintained in Escherichia coli strain DH5α [F$^-$80dlacZ M15 (lacZYA-argF)U169 recA1 endA1 hsdR17 ($r_k^-, m_k^+$) supE442$^-$ thi-1 gyrA1 relA1; Bethesda Research Laboratories, Gaithersburg, MD] or strain XL1-Blue [recA1 lac$^-$ endA1 gyrA96 thi hsdR17 supE44 relA1 (F'proAB lacIQ lacZ M15 Tn10); Stratagene, La Jolla, Calif.]

Cell Culture

L-M strain mouse fibroblasts were grown and subcultured regularly in suspension culture in YELP medium (yeast extract, lactalbumin hydrolyzate, peptone) supplemented with 3% fetal bovine serum (Microbiological Associates Incorporated, Bethesda, Maryland) as described previously (O'Callaghan et al., 1968, J. Virol. 2: 793–804 and O'Callaghan et al. 1968, Virology 36: 104–114). When radioactive precursors were employed, the cells were transferred to LP media (no yeast extract) supplemented with dialyzed calf serum.

Virus Propagation and Assay

The Kentucky A strain of equine herpes virus type 1, formerly known as equine abortion virus (EAV) and passaged from its hamster host to L cells in 1962 (Randall et al., 1962, Proc. Soc. Exp. Biol. Med. 110: 487–489), was employed. This virus (EHV-1L) has been passaged regularly in both suspension and monolayer cultures of L-M cells. For propagation of virus, cells either grown to confluency in monolayer cultures in 250-ml disposable plastic tissue culture flasks (Falcon Products, Cockeysville, Maryland) or maintained as log phase suspension cultures in 500-ml or 1000-ml Erlenmeyer flasks were employed. Infection was accomplished at a multiplicity of 5–10 plaque-forming units (PFU) per cell in a small volume of medium ($20\times10^6$ cell/ml); attachment was carried out for 2–2.5 hr at 37°.

The virus was assayed by using a modification of the plaque method of Garabedian et al. (1967, Proc. Soc. Exp. Biol. Med. 126: 568–571). Briefly, 0.1 ml aliquots of appropriate dilutions of the virus sample were added to monolayers of L–M cells in plastic petri dishes (60×15 mm; Falcon Products, Cockeysville, Maryland), which were then incubated at 37° for 2 hr in 5% $CO_2$ atmosphere to permit virus attachment. After this incubation, each monolayer was overlaid with 5 ml of chilled (4°) YELP medium containing 1.5% methyl cellulose 4000 cps (Fisher Chemical Company, Fair Lawn, N.J.), and the plates then were incubated at 37° for 4–5 days. The methyl cellulose overlay was removed by standing the plates at 4° for 30 min. and washing with ice cold phosphate-buffered saline (PBS; 0.02M sodium phosphate, 0.14M sodium chloride, pH 7.4). The monolayers then were fixed with 97% methyl alcohol (2 min.) and were stained with a 0.5% aqueous solution of methylene blue. Plaques could be counted macroscopically and were 0.75 to 1 mm in diameter. Microscopic examination showed plaques to be areas of cell-clearing due to formation of large syncytia; syncytia with as many as 100 or more nuclei were observed.

Neutralization of EHV-1 Infectivity by Antibodies

Two assays are available to ascertain whether antibodies or antisera have the ability to neutralize EHV-1 infectivity. First, a plaque reduction assay is available which quantitates EHV-1 neutralization and monitors its requirement for complement. This assay is time consuming, requiring approximately 6 days (O'Callaghan, et al., 1983. In *Herpesviruses*, B. Roizman, ed.; Series 2 of Comprehensive Virology, H. Frankel-Conrat and R. R. Wagner, eds. Plenum Publishing Corp., N.Y.: 215–318). A second assay is used for rapid analysis. This assay monitors EHV-1 encoded thymidine kinase (Tk) activity in $LTK^-$ cells to indicate neutralization. The ability of an antibody to prevent EHV-1 infection is measured by ability to inhibit induction of the viral Tk activity within the cell. This assay is described in detail below.

Dilutions of anti-EHV-1 gD antibodies or antisera are incubated with infectious EHV-1 (3 pFu/cell) for 1 hour at 37° C. and then added to monolayers of permissive $LTK^-$ cells. At 14 hr post infection, cell extracts are prepared and assayed for EHV-1 Tk activity by a rapid assay method (Wolcott, et al., 1989, Anal. Biochem. 178: 30–40). This method has been shown to detect and quantitate EHV-1 neutralizing antibodies with a sensitivity greater than or equal to the plaque reduction assay. However, this assay requires only one day to complete, in contrast to 6 days for the plaque reduction assay.

Vaccination of Hamsters, and Challenge with EHV-1

Suckling LSH Syrian hamsters are separated into groups of 10. One group receives a single inoculation of EHV-1 vaccine (i.e. purified EHV-1-gD protein or peptides derived therefrom). Inoculation may be by various routes, such as intramuscular, subcutaneous, or intraperitoneal. Another group receives a similar innoculation of EHV-1 vaccine as well as a booster on day 14. Another control group receives no vaccine. Additional groups are used if the effectiveness of varying amounts of vaccine is to be tested. Sera is collected from all hamsters at various intervals after inoculation and tested for neutralizing antibody in cell culture assays and for total anti-EHV-1 antibody by ELISA assay. All of the hamsters then receive a challenge of a known 50% lethal dose of a hamster-adapted Kentucky strain of EHV-1 by the intraperitoneal route 14 days after the last immunization. Survivors are counted at 7 days and 14 days after challenge with EHV-1 virus. Livers can be examined histopathologically for typical EHV-1 cytopathology. The efficacy of a EHV-1 vaccine is tested in horses in a similar manner.

Testing for Passive Immunization

This procedure is similar to the vaccination test described above. Hamsters are tested first, and then horses. Different groups of animals receive either no anti-EHV-1-gD antiserum or one or more injections of anti-serum. After 14 days all animals are challenged with EHV-1 virus, and the number of survivors are counted 1 week and 2 weeks after viral challenge.

Cloning and DNA Sequencing

The cloned 5.2 kbp BamHI M fragment containing the majority of $U_S$ sequences (Henry et al., 1981, Virology 115: 97–114; O'Callaghan et al., 1981. In *Developments in Molecular Virology, Vol. 1Herpesvirus RNA*, Y. Becker, ed.: 387–418) was used as the source of DNA for cloning and sequencing. Digestion of the BamHI M fragment with KpnI and XbaI yielded a 0.9 kbp BamHI/XbaI fragment, a 1.3 kb XbaI fragment, a 1.0 XbaI/KpnI fragment, and a 2.2 kb BamHI/KpnI fragment; these restriction endonuclease digestion products were ligated into the plasmid vectors pUC19 or pGEM-7Zf (Promega, Madison, Wis.) to generate the clones pCF, pCF2, pCF3, and pSZ-4, respectively (FIG. 1).

The 2.2 kb BamHI/KpnI subclone in pUC19, designated pSZ-4 and located at the left terminus of the BamHI M fragment, was selected for DNA sequence analysis. A nested set of deletions was generated for both strands according to the method of Henikoff (1984, Gene 28: 351–359) using the Erase-a-Base system (Promega, Madison, Wis.). After religation, the deleted plasmid DNA was used to transform competent *Escherichia coli* strain XL1-Blue (Stratagene, La Jolla, Calif.). Deletion clones were selected and sequenced using the dideoxy chain termination method (Sanger et al., 1977, Proc. Natl. Acad. Sci. USA 74: 5463–5467) as modified for use with T7 DNA polymerase (Pharmacia, Uppsala, Sweden) and $^{35}$S-dATP (Grundy et al., 1989, Virology 172: 223–236). 7-Deaza-dGTP was used in all sequencing reactions to reduce compression artifacts. Sequencing reactions were analyzed in 6% polyacrylamide wedge gels. Internal sequencing primers were synthesized and used to fill in gaps in the sequence. Both strands were completely sequenced.

DNA Sequence Analysis

DNA sequences were compiled using the programs of Staden (1980, Nuc. Acid. Res. 12: 505–519) and Eugene and Sam (Lark Sequencing Technologies). Searches of the Genbank and NBRF databases for sequences homologous to those of EHV-1 were performed with the FASTN/P programs of Lipman and Pearson (1985, Science 227: 1435–1440) using the IBI Pustell sequence analysis software. Analyses of DNA and protein sequence data were performed with the PC/GENE software package (Intelligenetics, Inc., Mountain View, Calif.).

EXAMPLE 2

DNA Sequence Analysis of Clone pSZ-4

The EHV-1 gD gene was identified by DNA sequence analysis of clone pSZ-4. The position of the pSZ-4 clone on the EHV-1 genome (map units 0.865–0.872 and 0.869–0.884) is shown in FIG. 1. pSZ-4 was generated by KpnI digestion of the 5.2 kbp BamHI M clone, a viral restriction fragment previously localized to the unique short ($U_S$) segment of the viral genome by Southern blot analysis (Henry et al., 1981, supra.). Sequence analysis of both strands of pSZ-4 (FIG. 2) revealed a total of 2,229 nucleotides with a base composition of 49.6% G+C. Analysis of the sequence for possible protein coding regions revealed one long open reading frame (ORF) which commenced with an ATG codon at nucleotides 511–513 (from the KpnI site) and extended 1,325 bases to a stop codon (TAA) at nucleotides 1837–1839. In addition to the start codon at 511–513, there are four in-frame ATG codons located at nucleotides 661–663, 679–681, 682–684, and 706–708. The start codon at 682–684 is the most favorable for initiation of translation according to Kozak's "leaky-scanning" model (Kozak, 1980, Cell 22: 7–8; Kozak, 1983, Microbiol. Rev. 47: 1045; and Kozak, 1986, Cell 44: 283–292S). The local nucleotide sequence of this initiation codon, TTATGATGG, shows alignment at positions −3 and +1, critical residues in Kozak's consensus motif, CC(A/G)CCATG(G). Initiation of protein synthesis from the first start codon (nucleotides 511–513) results in a primary translation product of 442 amino acids with a predicted molecular weight of 49,904; however, initiation from the fourth start codon (nucleotides 682–684) produces a polypeptide of 386 amino acids having a predicted molecular weight ($M_R$) of 43,206, a size comparable to those of HSV-1 gD (394 amino acids; $M_R$43,344; Watson et al., 1982, Science 218: 381–384; McGeoch et al., 1985, J. Mol. Biol. 181: 1–13), HSV-2 gD (394 amino acids; Watson 1983, Gene 26: 307–312) and PRY gp50 (402 amino acids; $M_R$44,500; Petrovskis et al., 1986, J. Virol. 59: 216–223). Furthermore, analysis of the translated sequence for a possible signal sequence revealed that residues following the fourth initiation methionine are most likely to serve as a signal sequence (see below).

Potential signals for the promotion and termination of transcription were identified within sequences flanking the gD ORF and include: (1) TATA motifs at nucleotides 328–331 and 561–564, (Corden et al., 1980, Science 209: 1406–1414) (2) CAAT box homologs at nucleotides 243–246 and 504–507, (Benoist et al., 1980, Nuc. Acid. Res. 8: 127–142;1 Efstratiadis et.m 1980, Cell 21: 653–668; Jones and Yamamoto, 1985, Cell 42: 559–572) (3) a polyadenylation consensus sequence (AATATA) 12 nucleotides downstream of the termination of translation (nucleotides 1848–1853) (Proudfoot and Brownlee, 1976, Nature 263: 211–214; Nordstrom et al., 1985, Proc. Natl. Acad. Sci. USA 82: 1094–1098), and (4) a GT-rich region at 1871–1876 (Birnstiel et al., 1985, Cell 41: 349–359). In addition, there are potential transcriptional regulatory sequences located in close proximity to the second TATA box. An AT-rich motif (572–578) was identified eight nucleotides downstream of the TATA box.

EXAMPLE 3

Identification of a EHV-1 Gene Product as a Member of the gD Family of Herpesvirus Glycoproteins To determine the relationship of the EHV-1 gD ORF gene product to other proteins, the translated sequence was compared to polypeptide sequences in the NBRF protein database using the amino acid homology algorithm, FASTP (Lipman and Pearson, 1985, Science 227: 1435–1440). Three protein sequences in the database displayed significant homology with the EHV-1 sequence and were HSV-1 gD (Watson et al., 1982, supra; McGeoch et al, supra), HSV-2 gD (Watson, 1983, supra) and the PRV gD homolog, gp50 (Petrovskis et al., supra). The results of this analysis (FIG. 3) revealed that the EHV-1 gD equivalent is 21% homologous with PRV gp50 and 18% homologous with HSV-1 gD and HSV-2 gD. A comparison of the sequences using the PAM 250 matrix (Dayhoff et al., 1978. In *Atlas of Protein Sequence and structure*, M. O. Dayhoff, ed.: 345–362) which permits alignment of conservative amino acid substitutions, indicated that a sequence similarity between the EHV-1 translated sequence and each of the three herpesvirus glycoproteins may be as high as 32%. The EHV-1 translated sequence contains 12 cysteine residues (amino acids 17, 35, 77, 80, 138, 176, 188, 197, 259, 273, 421, and 431), while PRV gp50 and HSV-1 gD and HSV-2 gD each contain seven cysteine residues (Watson et al., 1982, supra.; Watson, 1983, supra.; McGeoch et al., 1985, supra.; Petrovskis et al., 1986, supra.). The cysteine residues at positions 17 and 35 may not be part of the translated sequence if initiation of translation were to occur after the first start codon in the EHV-1 gD ORF. In the case of HSV-1 gD, six cysteine residues were judged to be essential for the proper conformation of the glycoprotein (Wilcox et al., 1988, J. Virol. 62: 1941–19747). Thus, these data indicate that the EHV-1 gD ORF (nucleotides 511–1839 depicted in FIG. 2), contained within clone pSZ-4, codes for a herpes viral polypeptide of the gD family.

EXAMPLE 4

Analysis of the EHV-1 gD Polypeptide Sequence

Figure 4:
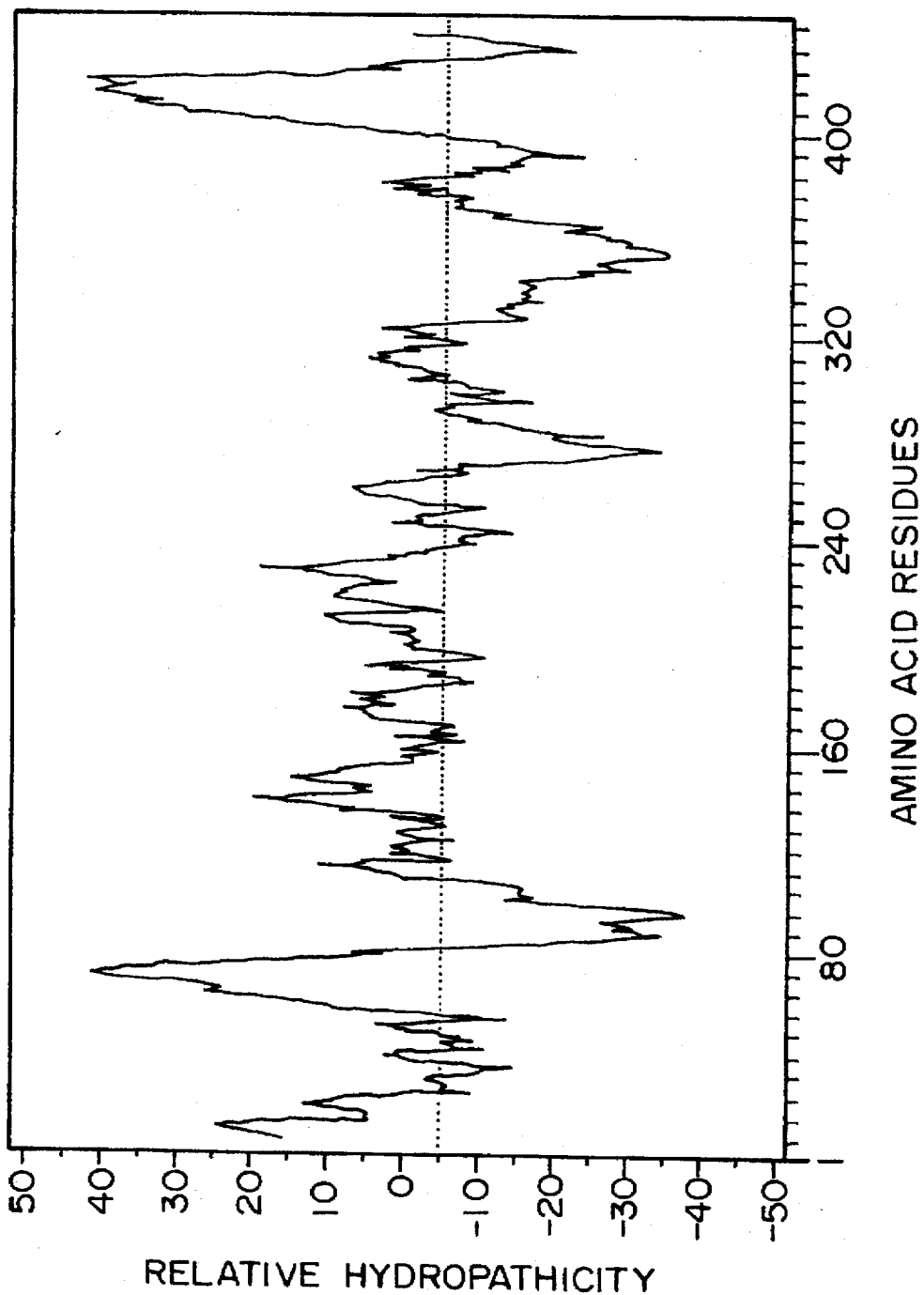

Analysis of the translated sequence revealed characteristics typical of a transmembrane glycoprotein. Hydropathicity plots using the algorithm of Kyte and Doolittle (1982, J. Mol. Biol. 157: 105–132) were used to identify hydrophobic domains within the EHV-1 gD amino acid sequence. Two strongly hydrophobic regions at the amino terminus spanning residues 1–21 and 58–76 (as depicted in FIG. 2) were candidates for a signal sequence (FIG. 4). Further analysis of these regions using the weight matrix algorithm of yon Heijne (1986, Nuc. Acid. Res. 14: 4683–4690) identified the second hydrophobic domain as the most likely sequence for a signal peptide. The signal sequence begins at the fourth methionine at amino acid position 58 in the translated sequence followed by the sequence AGR. The hydrophobic core begins at amino acid residue 62 and contains 15 hydrophobic amino acids, LVFAMAIAILSVVLS. The signal sequence cleavage site is predicted to occur after serine residue 76. The predicted signal sequence is 19 residues in length, and occurs in a position similar to that of HSV-1 gD (FIG. 4), and the mature polypeptide is 367 amino acids in length. Near the carboxyl terminus is a region (residues 394–422) enriched for hydrophobic amino acids and thus it may function as transmembrane anchor domain. Further analysis of this region using the method of Klein et al. (1985, Biochem. Biophys. Acta 815: 468–476) revealed residues 406–422 as possible membrane spanning amino acids. Assuming the primary translation product is processed to remove the signal peptide and that the polypeptide is anchored in the membrane, residues 77–406 are exposed on the surface of mature virions or infected cell membranes. The exposed region contains four consensus sequence motifs for the addition of N-linked oligosaccharides as indicated in FIG. 2 (N-X-S/T; Hubbard and Ivatt, 1981, Ann. Rev. Biochem. 50: 555–583). The putative carboxyl-terminal cytoplasmic domain spans residues 423–442, is enriched for hydrophilic amino acids, and possesses a net positive charge of 2.

EXAMPLE 5

Production and Purification of a EHV-1 gD-BETA-Galactosidase Fusion Protein

Expression of EHV-1 gD as a beta galactosidase fusion protein.

The EHV-1 gD protein is expressed as a fusion protein with beta-galactosidase using a lambda gt11 expression vector (Sambrook, et al., 1989, *Molecular Cloning: A Laboratory Manual* Vol. 2 Cold Spring Harbor Laboratory Press: 12.1–12.44). Fragments containing the EHV-1 gD open reading frame, or portions thereof, are fused in-frame with the beta-galactosidase open reading frame. This is accomplished by use of restriction enzyme digestion and exonuclease treatment to generate the appropriate EHV gD DNA fragment, followed by ligation to appropriately cut lambda gt11 DNA. These recombinant DNA molecules are packaged into lambda phage heads in vitro, and the resultant phage are used to transfect *E. coli* KM392 cells in the presence of 5-bromo-4-chloro-3-indolyl beta-D galactoside (×-gal). Under these conditions, phage harboring EHV-1 gD inserts appear as clear plaques (Benton and Davis, 1977, Science 196: 180). Alternatively the phage are plated on the *E. coli* host Y1090 since this strain contains: 1) genes for the lac repressor which prevents lacZ-directed gene expression until it is derepressed by the addition of IPTG (isopropyl-beta D thiogalactopyranoside), 2) a deficiency in the lon protease which prevents marked degradation of the EHV-1 fusion protein, and 3) supF to suppress the phage amber mutation for cell lysis [S100]. The recombinants are amplified in *E. coli* KM392 carrying the plasmid pMC9 which expresses the lac repressor (Calos et al. 1983, Proc. Natl. Acad. Sci. USA 80: 1266). For both recombinant hosts [KM392 (pMc9) or Y1090], plaque formation is initiated in the absence of any lacZ-directed expression to ensure that fusion proteins toxic to the host, do not inhibit the growth of any particular member of the library.

Purification of EHV-1 Polypeptide/Galactosidase Fusion Protein.

Since the lambda gt11 expression vector system produces a fusion protein consisting of both beta-galactosidase and EHV-1 epitopes, these characteristics are used to purify the EHV-1 gD polypeptide by employing anti-beta galactosidase antibody linked to Sepharose 4-B in an immunoaffinity column. Briefly, rabbit anti-beta galactosidase (IgG fraction; United States Biochemical Corporation, Cleveland, OH) is covalently linked to Sepharose 4B using the cyanogen bromide activation method. Anti-beta galactosidase (1–30 mg/ml) is dialyzed into an appropriate buffer and centrifuged (100,000 xG to remove aggregates). The CNBr-activated Sepharose is filtered, washed, and hydrated with ice cold 0.1 mM HCl. A weighed amount of activated Sepharose 4B (density —1.0) is added to an equal volume of antibody solution (10 mg/ml) and stirred overnight at 4° C. Glycine (0.05M) is added to saturate any remaining reactive group on the Sepharose 4B.

An EHV-1 gD fusion protein is obtained from *E. coli* Y1090 infected with recombinant gt11. LacZ directed expression of the fusion protein is induced in the presence of IPTG, and a lytic infection is initiated. The lysate from this infection is used for a batch purification of the fusion polypeptide. Briefly, the antibody-Sepharose complex is mixed with the lysate solution and the slurry is applied to a column. The column is washed 10 times with wash buffer (0.01M Tris, pH 8.0 0.14M NaCl, 0.025% $NAN_3$), and the purified fusion protien is eluted with high pH triethanolamine.

An EHV-1 gD fusion protein, purified by this method, is of sufficient purity for production of anti-EHV-1 gD antibodies.

EXAMPLE 6

Expression of EHV-1 gD in an pKK223-3 Prokaryotic Expression System

The pKK223-3 vector contains the strong trp-lac (tac) promoter first described by deBoer et al. (1983, Proc. Natl. Acad. Sci. USA). The tac promoter contains the −35 region of the trp promoter and the −10 region, operator, and the ribosome binding site of the lac UV-5 promoter. In a lac $i^Q$ host such as *E. coli* JM105, the tac promoter is repressed and may be derepressed at the appropriate time by the addition of IPTG. The tac promoter is followed by a polylinker derived from pUC8 (Vieria and Messing, 1982, Gene 17: 259–268) containing unique EcoRI, BamHI, SalI, PstI, SmaI, and HindIII restriction enzyme sites which facilitate the positioning of genes behind the promoter and ribosomal binding site. The polylinker is followed by a DNA segment containing the strong rrnB ribosomal RNA transcription terminators which have been previously characterized (Brosius et al., 1981, J. Mol. Biol. 148: 107; and Brosius et al., 1981, Plasmid 6: 112). The position of the terminators stabilizes the host-vector system, presumably by inhibiting the overexpression of detrimental RNA species or proteins by the strong tac promoter contained on the vector (Gentz et al., 1981, Proc. Nat. Acad. Sci USA 78: 4936; Brosius, 1981, supra,). The remainder of the plasmid consists of pBR322 sequences.

Expression of EHV-1 gD polypeptides within a pKK233-3 vector is induced by introduction of IPTG to the culture medium when using *E. coli* JM105 as host cells. An EHV-1 gD polypeptide is detected by comparison of the electrophoretic patterns of proteins derived from JM105 cells having the gD expression vector, with the pattern from cells that do not. SDS polyacylamide gels stained with an appropriate protein stain, such as Coomassie Blue, may be used for these comparisons, or, Western blot analysis using anti-EHV-1 gD antibodies to detect a gD polypeptide, may be employed (see for example Harlow, et al., 1988, *Antibodies: A Laboratory Manual*, Cold Spring Harbor Laboratory Press).

The gD polypeptide(s) expressed in a pKK233-3 expression vector system are purified by preparative SDS gel electrophoresis, or by immunoaffinity chromatography with an anti-EHV-1 gD antibody in a manner similar to that described in Example 5.

EXAMPLE 7

Expression of EHV-1 gD in A Baculovirus Expression System

To obtain regulated expression of an EHV-1 gD polypeptide, the coding region of the EHV-1 gD gene is placed downstream of a strong baculovirus promoter, the polyhedrin promoter, within a transfer vector. The transfer vector is a plasmid which has been genetically engineered to contain baculovirus DNA flanking the polyhedrin gene, as well as convenient restriction enzyme recognition sites adjacent to the strong polyhedrin promoter. Transfer vectors are co-transfected with baculovirus DNA to allow homologous recombination between the baculovirus DNA within the transfer vector and the genome of the baculovirus. Such homologous recombination replaces the polyhedrin coding region in the baculovirus genome with the EHV-1 gD coding region. This replacement causes the polyhedrin gene product to be lost and gives rise to an occlusion negative viral phontype. Hence, baculoviruses which have incorporated the EHV-1 coding region are recognized by an occlusion negative phenotype. Techniques for distinguishing this phenotype, as well as for manipulating transfer vectors, and recombinant baculoviruses are provided in Summers et al. (1987) *A Manual of Methods for Baculovirus Vectors and Insect Cell Culture Procedure*, Texas Agricultural Experiment Station, Bulletin No. 1555.

To place the EHV-1 gD coding region into a transfer vector, pSZ-4 DNA is digested with the appropriate restriction emzymes and the DNA fragment encoding EHV-1 gD amino acids 1–386 (or any portion thereof) is isolated. The transfer vector, pac373, is digested with a restriction enzyme that cuts just downstream of the polyhedrin promoter. After ligation (T4 DNA ligase, New England Biolabs) of the fragment encoding the EHV-1 gD coding region to the linearized transfer vector, recombinants are selected for ampicillin resistence and restriction mapped to identify those having the correct structure.

The recombinant EHV-1 gD transfer vector is co-transfected with baculovirus AcMNPV DNA, into *S. frugiperda* Sf9 cells by the method described in Summers et al. The plaques are screened for an occlusion negative phenotype, and several recombinant (occlusion-negative) baculovirus clones areseparately plaque purified three times to ensure that the EHV-1 gD recombinant clones are homogeneous.

EXAMPLE 8

Generation of Polyclonal Antibodies

To prepare polyclonal antibodies directed against EHV-1 gD polypeptides, any of a variety of antigens are used, such as a purified EHV-1 gD fusion protein, a purified EHV-1 gD polypeptide or a synthetic peptide encoding a portion of a gD polypeptide.

Synthetic peptides with the following amino acid sequences were made for immunization into rabbits:

1) Amino acids 80–98 (as depicted in FIG. 2):

$NH_2$-Cys-Glu-Lys-Ala-Lys-Arg-Ala-Val-Arg-Gly-Arg-Gln-Asp-Arg-Pro-Lys-Glu-Phe-Pro-COOH

2) Amino acids 343–361 (as depicted in FIG. 2):

$NH_2$-Glu-Ile-Thr-Gln-Asn-Lys-Thr-Asp-Pro-Lys-Pro-Gly-Gln-Ala-Asp-Pro-Lys-Pro-Asn-Cys-COOH

These EHV-1 gD peptides were identified as strongly antigenic epitopes for all EHV-1 gD polypeptides by computer analysis of the EHV-1 gD polypeptide sequence. Peptide 2 has an additional cysteine residue on its carboxy terminus to facilitate coupling to a carrier protein.

New Zealand white female rabbits were immunized by subdermal injection with 100 µl of Freund's complete adjuvant containing 0.1–1 mg of oligopeptide in multiple locations along the back. The rabbits were first shaved on both sides of the back for easy subdermal injection. Typically rabbits were boosted with similar amounts of antigen at 10–40 days intervals following the primary injection, until the serum was positive for gD reactivity at a dilution of greater than $10^{-4}$ when assayed by ELISA, immunoblotting, and immunoprocipitation analysis.

EXAMPLE 9

Preparation of Horse Anti-EHV-1-gD Antisera

Horses are immunized with the entire EHV-1 gD protein, or portions thereof (i.e. the peptides of Example 8) or an EHV-1 gD fusion protein, to create an antisera reactive against EHV-1. This antisera is useful for treatment or prevention of EHV-1 infection. The procedure employed is analogous to that for making polyclonal antibodies (Example 8).

To enhance the immune reaction the antigen is placed in an adjuvant before immunization. An adult horse is injected with 50 µg to 100 mg of an gD antigen. Immunization is intramuscular, intradermal or subcutaneous. Multiple sites of injection are generally used with subcutaneous or intradermal immunization to stimulate the immune response. After primary immunization the animal is boosted about every 2–6 weeks.

Horse serum is drawn after one or more boosting injections and tested for high anti-EHV-1-gD antibody titers by the virus neutralization assay, and for the ability to alleviate EHV-1 infection, first in hamsters and then in horses.

EXAMPLE 10

Monoclonal Antibody Production

Monoclonal antibodies are prepared in accordance with the techniques developed by Kohler and Mulskin (*Eur. J. Immunol.* 6: 511–519, 1976) and Harlow et al. (*Antibodies: A Laboratory Manual*, Cold Spring Harbor Laboratory Press, 1988). Balb/c mice are immunized subdermally with 100 ul of Freund's complete adjuvant containing 0.1–1 mg of am EHV-1 gD antigen such as a purified EHV-1 gD polypeptide or fusion protein, or the conjugated or non-conjugated EHV-1 peptides described in Example 8. Two weeks after the initial injection, the mice are boosted with the appropriate antigen by intravenous and intraperitoneal injection of about 100 ug of antigen in phosphate buffered saline (PBS).

Five days after the last injection and after confirmation of the presence of antibody in mouse sera, the mice are sacrificed and their spleens removed. Spleen cells are obtained by gentle disruption of the spleen in a 7 ml Dounce homogenizer in 3.5–4 ml PBS. The cells are then pelleted at 1200 rpm in a PR6 centriguge for 6 minutes at room temperature. The supernatant is removed into a suction flask, and the cells are resuspended in 15 ml 0.83% $NH_4Cl$. The cells are again pelleted by centrifuation for 8 minutes, at 1200 rpm at room temperature, then the supernatant is withdrawn into a suction flask cells resuspended in 20 ml PBS.

The following solutions are prepared for use in the subsequent cell fusion:

Hypoxanthine (H), 680 mg/100 ml $H_2O$; add 204 drops conc. $H_2SO_4$; heat to dissolve Aminopterin (A), 46.4 mg/100 ml $H_2O$; add 2 drops 1.0 N NaOH to dissolve Thymidine (T), 775 mg/100 ml $H_2O$; add 45 mg glycine PEG-DME-melt PEG at 42° C., then add 1 ml DME (at 37° C.); adjust pH with 1.0N NaOH to 7.6

DMEM—to 500 ml DME add 37.5 ml a- horse serum; 37.5 ml FCS, 10.0 ml L-glutamine, 0.2 ml garamycin, 2X HAT-DME—to 200 ml DME add 25.0 ml a- horse serum, 25.0 ml FCS, 4.0 ml L-glutamine, 0.2, garamycin, 0.8 ml H, and 0.8 ml A, and 0.8 mlT (2X HT-DME omits A)

Cloning Agar-350 mg unwashed Difco agar in 25 ml $H_2O$, autoclaved

Cloning Medium—to 25 ml 2X DME, add 35 ml filtered, condition DMEM, 7 ml a- horse serum, 7 ml FCS, 1 ml L-glutamine, 0.1 ml garamycin.

Two 30 ml flasks of X63-Ag8.653 myeloma cells are added to centrifuge tubes and spun down at 1200 rpm for 8 minutes at room temperature. The spleen cells are resuspended in 20 ml PBS. From each suspension, 0.01 ml is removed and added to 0.1 ml 0.4% trypan blue and 0.3 ml PBS for cell counting. The volume of each suspension is adjusted so as to obtain a spleen cell to X63-Ag8.653 cell ratio of 10: 1, and the suspensions are then mixed. The mixture is pelleted at 1200 rpm for 8 minutes at room temperatue and all but about 0.1 ml of supernatant removed. The cells are then resuspended in the remaining liquid and added to 1.3 ml of 1: 1 PEG-DME solution, pH 7.6. Every minute the volume of the solution is doubled with DME until the final volume is 25 ml.

The cells are again pelleted, the supernatant decanted, and the cells resuspended in enough 50% 2X HAT-DME/50% condition DMEM (the supernatant retained #from the X63-Ag8.653 cells above) to yield a final concentration of about $3.5 \times 10^6$ spleen cells. The cells are distributed into a 96-well flat-bottom microtiter plate (TC-96; Flow Laboratories), at 0.1 ml/well. The plate is incubated at 37° C. in humidified air/$CO_2$ until visible colonies appear, usually about 10–12 days. The contents of the well is transferred to 0.5 ml of HAT-DME/conditioned DME in a TC-24 plate (Flow Laboratories). When healthy cell growth appears (about 2–5 days), about 0.35 ml medium is removed and tested for antibody production by enzyme-linked immunosorbent assay (ELISA), immunoprecipitation of EHV-1 gD polypeptides, or Western blot analysis. When cells producing the antibodies of interest are growing well, one drop of each culture is transferred into 1.0 ml DMEM in a TC-24.

To clone the hybrid cells, 25 ml of melted agar and 76 ml of cloning medium is combined, and 5 ml is pipetted into 60 mm petri dish and left to solidify. Cells from DMEM cultures are diluted in 50% DMEM/50% conditioned DMEM, at $10^{-1}$ or $10^{-2}$ dilutions depending on cell growth. Into sterile tubes is placed 0.1 ml of each of the two dilutions, and to each is added 0.9 ml of cloning medium/agar mixture. This is mixed well and poured over the surface of the agar underlay. After solidification the plates are incubated at 37° C. in a $CO_2$ incubator until colonies are visible with the naked eye, typically about 7–10 days. Colonies are then picked and transferred 0.1 ml of DMEM/conditioned DMEM in a TC-99 plate and incubated at 37° C. in a $CO_2$ incubator. After the culture is acidic (usually 1–4 days), transfer is made to 0.05 ml DMEM in TC-24 plate. When the growth is 50% confluent, the medium is removed and tested for antibody production as previously. Those clones producing EHV-1 gD specific antibodies are moved into 5 ml DMEM in 25 $cm^2$ flasks. Cloned cells are then frozen or injected into mice for ascites production.

We claim:

1. An isolated peptide comprising a portion of the sequence of Equine Herpes Virus-1 gD, wherein the portion comprises the sequence of amino acids 80–98 of FIG. 2.

2. An isolated peptide comprising a portion of the sequence of Equine Herpes Virus-1 gD, wherein the portion comprises the sequence of amino acids 343–362 of FIG. 2.

3. An isolated polypeptide comprising amino acids 1–442 of the Equine Herpes Virus-1 gD polypeptide of FIG. 2.

4. An isolated polypeptide comprising amino acids 51–442 of the Equine Herpes Virus-1 gD polypeptide of FIG. 2.

5. An isolated polypeptide comprising amino acids 57–442 of the Equine Herpes Virus-1 gD polypeptide of FIG. 2.

6. An isolated polypeptide comprising amino acids 58–442 of the Equine Herpes Virus-1 gD polypeptide of FIG. 2.

7. An isolated polypeptide comprising amino acids 77–442 of the Equine Herpes Virus-1 gD polypeptide of FIG. 2.

8. An immunogenic composition comprising the peptide of claim 1 and a pharmaceutically acceptable carrier.

9. An immunogenic composition comprising the peptide of claim 2 and a pharmaceutically acceptable carrier.

10. An immunogenic composition comprising the polypeptide of claim 3 and a pharmaceutically acceptable carrier.

11. An immunogenic composition comprising the polypeptide of claim 4 and a pharmaceutically acceptable carrier.

12. An immunogenic composition comprising the polypeptide of claim 5 and a pharmaceutically acceptable carrier.

13. An immunogenic composition comprising the polypeptide of claim 6 and a pharmaceutically acceptable carrier.

14. An immunogenic composition comprising the polypeptide of claim 7 and a pharmaceutically acceptable carrier.

* * * * *

UNITED STATES PATENT AND TRADEMARK OFFICE
CERTIFICATE OF CORRECTION

PATENT NO. : 5,707,629
DATED : January 13, 1998
INVENTOR(S) : Dennis J. O'Callaghan It is certified that error appears in the above-identified patent and that said Letters Patent is hereby corrected as shown below:

Column 1, line 8, insert the following as a new paragraph: --This invention was made with government support under AI-22001 and 89-37266-4735 awarded by the National Institutes of Health and the U.S. Department of Agriculture. The Government has certain rights in the invention.--

Column 2, lines 3-5: delete "inverting in orientation, giving rise to the prototype and"

Column 3, line 64: "re,eat" should read --repeat--

Column 4, line 27: "glo50" should read --gp50--

Column 4, line 56: "libary" should read --library--

Column 4, line 65: "IPRV)" should read --(PRV)--

Column 7, line 44: "immunaprecipitation" should read --immunoprecipitation--

Column 8, line 41: delete "e5"

Column 9, line 34: "immunogllubulins" should read --immunoglobulins--

Column 11, line 15: "glutaraldehye" should read --glutaraldehyde--

Column 11, line 44: delete "D"

UNITED STATES PATENT AND TRADEMARK OFFICE
CERTIFICATE OF CORRECTION

Page 2 of 2

PATENT NO. : 5,707,629
DATED : January 13, 1998
INVENTOR(S) : Dennis J. O'Callaghan It is certified that error appears in the above-identified patent and that said Letters Patent is hereby corrected as shown below:

Column 12, line 57: "does" should read --dosages--

Column 17, line 32: "PRY" should read --PRV--

Column 18, line 41: "yon" should read --von--

Column 20, line 4: "protien" should read --protein--

Column 21, line 33: "areseparately" should read --are separately--

Column 22, line 45: "centriguge" should read --centrifuge--

Column 22, line 48: "centrifuation" should read --centrifugation--

Column 23, line 22: "#from" should read --from--

Column 23, line 24: "106" should read --$10^6$--

Signed and Sealed this

Twenty-seventh Day of June, 2000

Attest:

Attesting Officer

Q. TODD DICKINSON

Director of Patents and Trademarks